United States Patent
Graham

(10) Patent No.: US 11,205,504 B2
(45) Date of Patent: Dec. 21, 2021

(54) SYSTEM AND METHOD FOR COMPUTERIZED SYNTHESIS OF SIMULATED HEALTH DATA

(71) Applicant: CARDINAL HEALTH COMMERCIAL TECHNOLOGIES, LLC, Dublin, OH (US)

(72) Inventor: Jeffrey Nathan Graham, Sunbury, OH (US)

(73) Assignee: CARDINAL HEALTH COMMERCIAL TECHNOLOGIES, LLC, Dublin, OH (US)

( * ) Notice: Subject to any disclaimer, the term of this patent is extended or adjusted under 35 U.S.C. 154(b) by 224 days.

(21) Appl. No.: 16/226,368

(22) Filed: Dec. 19, 2018

(65) Prior Publication Data

US 2020/0202987 A1 Jun. 25, 2020

(51) Int. Cl.
*G16H 10/60* (2018.01)
*G06N 7/00* (2006.01)
*G16H 50/20* (2018.01)

(52) U.S. Cl.
CPC ............. *G16H 10/60* (2018.01); *G06N 7/005* (2013.01); *G16H 50/20* (2018.01)

(58) Field of Classification Search
None
See application file for complete search history.

(56) References Cited

U.S. PATENT DOCUMENTS

2008/0004904 A1 1/2008 Tran

FOREIGN PATENT DOCUMENTS

WO WO-2014120204 A1 * 8/2014 ............ G06F 19/00

OTHER PUBLICATIONS

Synthea: An approach, method, and software mechanism for generating synthetic patients and the synthetic electronic health care record, Journal of the American Medical Informatics Association, available at https://www.researchgate.net/publication/319454272_Synthea_An_approach_method_and_software_mech (Year: 2017).*

* cited by examiner

*Primary Examiner* — Rachelle L Reichert
(74) *Attorney, Agent, or Firm* — Arent Fox LLP

(57) ABSTRACT

Systems and methods related to the computerized synthesis of simulated health data are provided. A computing device can receive a respective data model constructed from protected health information (PHI) hosted by a respective health data provider. The computing device can create a state transition machine from the received data model, where a state of the state transition machine represents a health related event of a synthetic life. The computing device can generate a synthetic health data set for each synthetic person in a synthetic population by calculating one or more health related events for each time step in the synthetic life. The computing device can calculate a similarity score by comparing the generated synthetic health data set to an actual health data set. The computing device can adjust the received data model based on the score falling below a threshold similarity, thereby creating an adjusted data model.

20 Claims, 10 Drawing Sheets

```
800
  802 →    "resource" : {
            "resourceType" : "Condition",
  804 →    "id" : "757f27b1-debf-4027-952f-70171984f7f5",
            "clinicalStatus" : "active",
            "verificationStatus" : "confirmed",
               "code" : {
               "coding": [
                  {
  806 {            "system : "http://snomed.info/sct",
                   "code": "64859006",
                   "display": "Sinus Infection"
                  }
               ]
            },
  808 {    "subject": {
              "reference": "urn:uuid:b7cc2c2f-0eb6-4299-aa64-3b4dc11a27e1"
            },
  810 →    "onsetDateTime": "1991-02-07T20:27:27-05:00",
            }
```

FIG. 8

SYSTEM AND METHOD FOR COMPUTERIZED SYNTHESIS OF SIMULATED HEALTH DATA

BACKGROUND

In the field of healthcare, electronic health record (EHR) data refers to digital collections of patient and population health information across time. Depending on the source, EHR may include a variety of metrics such as demographics, medical history, laboratory results, and billing information. EHR data provides an extensive data source for healthcare research and quality improvement. For example, policy researchers may evaluate the spread of an epidemic across a region to identify future emergency response strategies. In other cases, a large hospital may improve patient care by identifying the best practices to treat a particular disease. Many other potential benefits of using EHR data for research exist.

In practice, EHR data frequently includes or is associated with Protected Health Information (PHI) data. PHI data may include any information that links health status, payment, or treatment to a specific individual. For example, PHI data may include names, geographical identifiers, dates, and health insurance numbers. Due to government regulations such as the Health Insurance Portability and Accountability Act (HIPAA) in the United States, General Data Protection Regulation (GDPR) in the European Union, or the Personal Information Protection and Electronic Documents Act (PIPEDA) in Canada, PHI data is often required to be removed or de-identified from EHR data before use of the EHR data, to preserve the privacy of healthcare patients.

De-identification methods such as k-anonymization are known and have been widely used to disassociate PHI data by ensuring that data from at least K individuals are undistinguishable. However, poor implementation of anonymization schemes, lack of widespread privacy guidelines, and inadvertent cybersecurity leaks of original PHI data can place organizations using EHR data at great regulatory risk. Moreover, many types of healthcare research, such as epidemiology, may require unaltered PHI data to gain insight onto individual patient outcomes. However, this may cause the difficulty of going through Institutional Review Boards (IRB) and further creates a risk of PHI data leaks.

In addition to the complexity of PHI regulations and de-identification, the integration of data across multiple EHR sources has many technical challenges. EHR records are not always in consistent format across EHR providers, making data transformation and aggregation difficult. Tracking individual patients that frequently change healthcare providers may be impossible without access to any PHI identification attributes. Without evidence of a robust software system that can mitigate cybersecurity threats, healthcare organizations may be reluctant to share EHR data in fear of PHI data risks.

Additionally, with the growing field of computer driven health models, EHR data may not provide researchers with sufficient information to analyze complex health outcomes. For example, due to inconsistencies in healthcare visits, EHR data may be time limited and only extend over the period of a few years, thus affecting any models that extend over a patient's lifetime. Also, the amount of EHR data may be limited for rare diseases or conditions or nonexistent for unknown diseases and comorbidities. In these cases, it may be difficult to rely on EHR data to predict complex events or to extrapolate the health outcomes of patient populations over a lifetime.

Consequently, a need exists for a system to address the shortcomings of using EHR data in medical research and quality improvement.

SUMMARY

In one aspect, a method is disclosed. The method includes a computing device for (1) receiving at least one respective data model constructed at least in part from protected health information (PHI) hosted by a health data provider of a plurality of health data providers, the received data model containing no PHI, (2) creating at least one state transition machine from the at least one received data model, where a state of the at least one state transition machine represents a health related event of a synthetic life and where a probability of transitioning from a first state to a second state is based on at least one health attribute and at least one disease prevalence statistic, (3) generating a synthetic health data set comprised of a synthetic electronic health record (EHR) for each synthetic person in a synthetic population, where the synthetic EHR for each synthetic person is generated by calculating one or more health related events for each time step in the synthetic life and where the one or more health related events are determined in part by the health attributes of each synthetic person at each time step, (4) calculating a similarity score by comparing the generated synthetic health data set to an actual health data set, where the actual health data set includes at least one health related event and associated time information for that at least one health related event, the at least one health related event and associated time information derived from at least a portion of the PHI hosted by the health data provider, and (5) adjusting the at least one received data model based on the score indicating similarity falling below a threshold similarity, thereby creating at least one adjusted data model.

In another aspect, a computing system is disclosed. The system includes at least one health data repository constructed from protected health information (PHI) hosted by a health data provider of a plurality of health data providers. The system further includes a computing device containing at least one received data model constructed from the at least one health data repository, where the at least one received data model contains no PHI. The system also includes at least one state transition machine that is (1) constructed from the at least one received data model, where a state of the at least one state transition machine represents a health related event of a synthetic life and where a probability of transitioning from a first state to a second state is based on at least one demographic and at least one health attribute and at least one disease prevalence statistic, and (2) configured to generate a synthetic health data set comprised of a synthetic electronic health record (EHR) for each synthetic person in a synthetic population, where the synthetic EHR for each synthetic person is generated by calculating a one or more health related events for each time step in the synthetic life, where the one or more health related events are determined in part by the health attributes of each synthetic person at each time step. The system also includes a processor configured to (1) calculate a similarity score by comparing the synthetic health data set to an actual health data set, wherein the actual health data set includes at least one health related event and associated time information for that at least one health related event, the at least one health related event and associated time information derived from at least a portion of the PHI hosted by the health data provider, and (2) adjust the at least one received data model based on the score indicating similarity falling below a threshold similarity, thereby creating at least one adjusted data model.

In yet another aspect, a non-transitory computer readable medium is provided. The non-transitory computer readable medium has stored thereon instructions, that when executed by one or more processors of a computing device, cause the computing device to perform functions. The functions include: (1) receiving at least one respective data model constructed at least in part from protected health information (PHI) hosted by a health data provider of a plurality of health data providers, the received data model containing no PHI, (2) creating at least one state transition machine from the at least one received data model, where a state of the at least one state transition machine represents a health related event of a synthetic life and where a probability of transitioning from a first state to a second state is based on at least one health attribute and at least one disease prevalence statistic, (3) generating a synthetic health data set comprised of a synthetic electronic health record (EHR) for each synthetic person in a synthetic population, where the synthetic EHR for each synthetic person is generated by calculating one or more health related events for each time step in the synthetic life and where the one or more health related events are determined in part by the health attributes of each synthetic person at each time step, (4) calculating a similarity score by comparing the generated synthetic health data set to an actual health data set, where the actual health data set includes at least one health related event and associated time information for that at least one health related event, the at least one health related event and associated time information derived from at least a portion of the PHI hosted by the health data provider, and (5) adjusting the at least one received data model based on the score indicating similarity falling below a threshold similarity, where adjusting the at least one received data model comprises representing the at least one received data model as at least one probabilistic graphical model and determining probabilities of the at least one probabilistic graphical model based on at least one health related event from the actual health data set, thereby creating at least one adjusted data model.

The foregoing summary is illustrative only and is not intended to be in any way limiting. In addition to the illustrative aspects, embodiments, and features described above, further aspects, embodiments, and features will become apparent by reference to the figures and the following detailed description and the accompanying drawings.

BRIEF DESCRIPTION OF THE DRAWINGS

FIG. 8 depicts example output EHR data that is generated from a synthetic EHR generator, in accordance with example embodiments.

DETAILED DESCRIPTION

Figure 1:
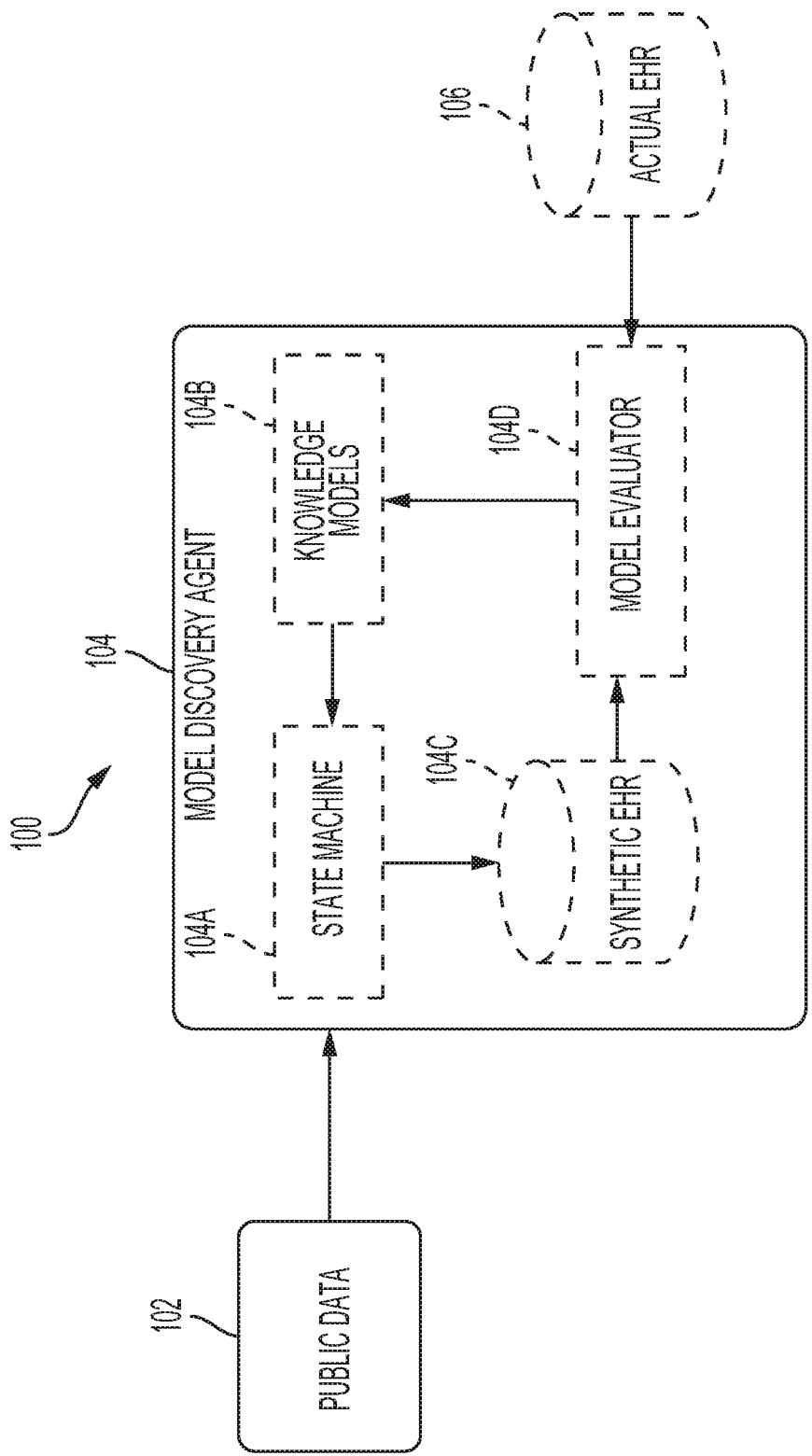
FIG. 1 depicts a simplified block diagram of a synthetic EHR system, in accordance with example embodiments.

Example methods and systems are described herein. Any example embodiment or feature described herein is not necessarily to be construed as preferred or advantageous over other embodiments or features. The example embodiments described herein are not meant to be limiting. It will be readily understood that certain aspects of the disclosed systems and methods can be arranged and combined in a wide variety of different configurations, all of which are contemplated herein.

Furthermore, the particular arrangements shown in the Figures should not be viewed as limiting. It should be understood that other embodiments might include more or less of each element shown in a given Figure. Further, some of the illustrated elements may be combined or omitted. Yet further, an example embodiment may include elements that are not illustrated in the Figures.

I. Introduction

Embodiments of the systems and methods described herein can be used to generate synthetic healthcare data without PHI risk for use in healthcare policy and research. In some embodiments, census data, health incident statistics, medical coding dictionaries, and clinical practice guidelines are combined to create a simulation that models various diseases and medical conditions that occur over a patient lifespan (i.e. a synthetic life). In some embodiments, the simulation model is represented by one or more state transition machines in which states represent one or more health related events and the transitions represent probability of a synthetic patient progressing into another health related event based on the current patient state. Using the one or more state transition machines, hundreds, thousands, and/or millions of synthetic patient lives can be simulated, each producing synthetic EHR data representing the clinical conditions, diseases, treatments, and health outcomes during the synthetic life.

The embodiments described herein further compare synthetic EHR data to actual EHR data to determine the representativeness of the synthetic EHR data in regards to a population of interest. In some embodiments, univariate analysis is used to generate a similarity score between synthetic EHR data and actual EHR data. If the similarity score is below a predefined threshold, the one or more state transition machines may be adjusted (or readjusted) to generate more representative synthetic EHR data. The process of simulating and adjusting can be done again and again until the one or more state transition machines produce a representative synthetic data set with a similarity score meeting the threshold requirements.

Whereas using actual EHR data in research poses PHI risk or requires complex patient de-identification, the systems and methods described herein utilize machine learning techniques to statistically mirror multiple disease states within a population of interest, resulting in no PHI risk. As a result, the embodiments described herein provide an improvement to an area of healthcare policy and research technology.

II. Example Architecture

A. System Overview

FIG. 1 is a simplified block diagram of a synthetic EHR system 100, in accordance with the example embodiments. Synthetic EHR system 100 may use machine learning techniques to train one or more machine learning models to recognize patterns, provide predictions, and determine weights and measures during transition states of those predictions. Such machine learning models may be trained automatically or by acting on tuning parameters via interaction with an operator. The resulting trained machine learning models may be utilized to generate representative synthetic EHR data. In the example embodiments, synthetic EHR system 100 may include public data source 102, model discovery agent 104, and actual EHR data storage 106.

Public data source 102 may include, for example, census data or similar demographic information, health incident statistics, clinical practice guidelines (CPG) or similar diagnostic and treatment protocols, and medical coding dictionaries or similar medical term translation tools. Public data source 102 may be a collection of separate data sources hosted by different data providers or may be an aggregated data source hosted by a single data provider.

Model discovery agent 104 may be a collection of computerized devices used to generate representative synthetic EHR data by one or more machine learning models. Model discovery agent 104 may include, for example, state machine 104A, knowledge model 104B, synthetic EHR storage 104C, and statistical comparison engine 104D.

State machine 104A may include processes to simulate one or more synthetic lives. These processes may include generating a synthetic population from input population data, simulating synthetic lives for each synthetic person in the synthetic population, and outputting health details (i.e. synthetic EHR data) of each synthetic life. To simulate one or more synthetic lives, state machine 104A may be configured with one or more machine learning models, including, but not limited to: a neural network, a Bayesian network, a hidden Markov model, a Markov decision process, set/graph theory models, or other similar graphical models. Output from state machine 104A may be transmitted to synthetic EHR storage 104C.

Knowledge models 104B may include one or more clinical pathways representing known sequences of health related events that a patient may experience for a given health condition. For example, knowledge model 104B may include a clinical pathway for heart disease. One sequence of events for this pathway may include an initial cardiac arrest, followed by a hospital admission, followed by an open heart surgery. Another sequence of events for this pathway may include an initial cardiac arrest, followed by a hospital admission, and followed by a prescription drug treatment plan. The particular sequence of events that a patient experiences for a given health condition may be based in part on health attributes of the patient (e.g. weight, age, past medical history).

In some embodiments, knowledge models 104B may be auto generated or manually generated by model evaluator 104D from source data, such as public data 102 or actual EHR data 106. Knowledge models 104B may be stored in a flat file format (e.g. JSON) or in a document database disposed within model discovery agent 104. Knowledge models 104B may directly influence the configuration of state machine 104A in accordance with the embodiments herein.

Synthetic EHR storage 104C may include, for example, one or more databases to store synthetic EHR data generated by state machine 104A. For example, synthetic EHR storage 104C may include a column store database to store the synthetic EHR data.

Model evaluator 104D may include one or more processes to adjust knowledge models 104B based on the representativeness of the synthetic EHR data generated by state machine 104A. For example, model evaluator 104D may include a statistical comparison engine to compare data from synthetic EHR storage 104C to data from actual EHR storage 106. Based on the comparison, model evaluator 104D may utilize a tuning engine to adjust knowledge model 104B in accordance with the embodiments herein. In some embodiments, model evaluator may include one or more graph databases to compute adjustments to knowledge model 104B.

Actual EHR storage 106 may include, for example, one or more databases to store actual EHR data representative of a population of interest. For example, Actual EHR data storage 106 may include a column store database to store the actual EHR data. In example embodiments, the data in actual EHR storage 106 may be supplied by a health data provider.

Components of synthetic EHR system 100 may be configured across a variety of separate computing devices within a computer network. In some embodiments, multiple instances of synthetic EHR system 100 may be run on the computer network and the representative synthetic EHR data generated from each synthetic EHR system 100 on the computer network may be aggregated together.

B. Example Devices

Figure 2:
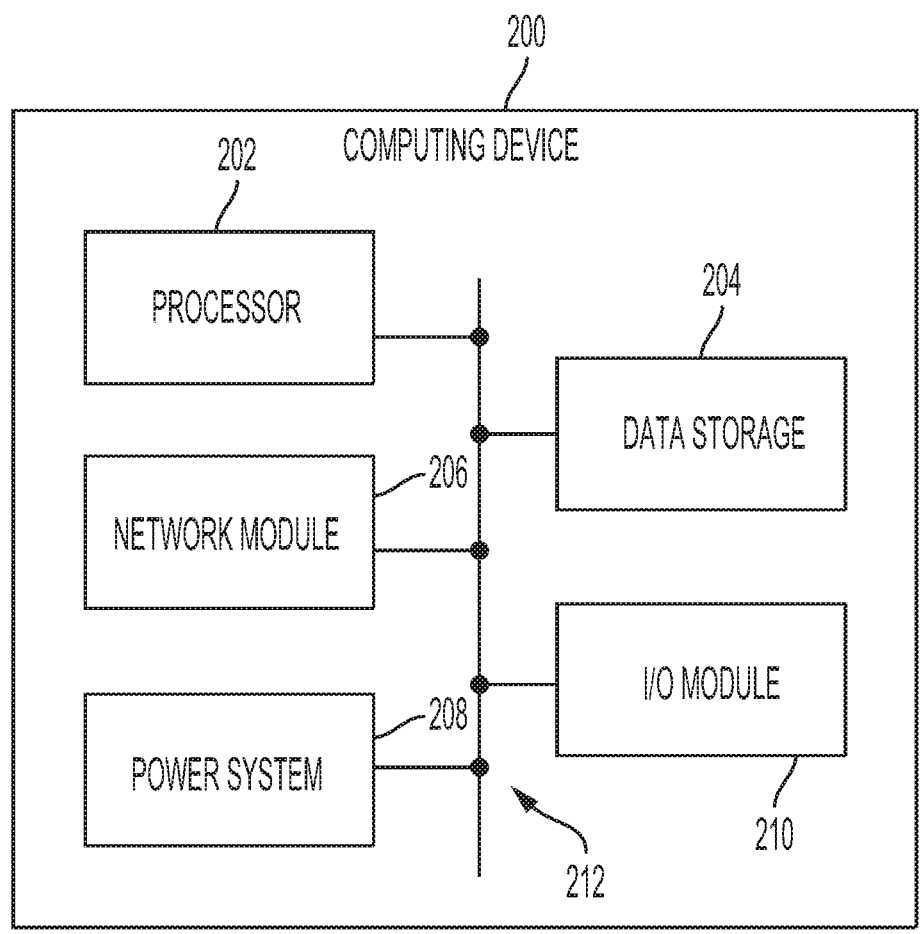
FIG. 2 depicts a simplified block diagram of an example computing device, in accordance with example embodiments.

FIG. 2 is a simplified block diagram of an example computing device 200, in accordance with the example embodiments. In the example embodiments, computing device 200 can be configured to perform one or more acts and/or functions related to public data source 102, model discovery agent 104, and/or actual EHR data storage 106. Computing device 200 may include various components, such as a processor 202, data storage 204, a communication module 206, input/output module 208, and/or a power system 210. Each of these components may be linked together via connection mechanism 212. In some embodiments, computing device 200 may include other components or devices (e.g., printers, detachable storage, etc.) to facilitate additional functions and/or interactions.

Connection mechanism 212 may be any mechanism that facilitates communication between two or more components, devices, or other entities. For example, the connection mechanism may be a cable, system bus, a packet-based communication network (e.g., the Internet), or a wireless medium.

Processor 202 may be one or more general-purpose processors and/or one or more special-purpose processors (e.g., a digital signal processor (DSP), graphics processing units (GPUs), etc.). Processor 202 can execute program instructions included in the data storage 204, as discussed below. Processor 202 may include register memory for temporarily storing the program instructions being executed and related data, as well as cache memory for temporarily storing recently used program instructions and related data.

Data storage 204 may include one or more volatile (e.g., random access memory (RAM)), non-volatile (e.g., read only memory (ROM), flash memory, hard disk drives, solid state drives), removable, and/or non-removable storage components. Data storage 204 may include firmware to boot or initiate some or all of computing device 200. Data storage 204 may also include a kernel, which may be part of an operating system, including modules for memory management, device drivers, scheduling processes, input/output, and communication. Data storage 204 may also include one or more user-space software programs, such as video players, as well as any libraries used by these programs.

Data storage 204 may store program instructions and/or data on a non-transitory, computer-readable medium. Data storage 204 may be integrated with processor 202 such that program instructions are executable by processor 202 to carry out any one or more methods, processes, or functions, such as those disclosed in this specification or the accompanying drawings.

Network module 206 may be one or more devices to allow the computing device 200 to connect with and/or communicate with other entities via one or more networks. Network module 206 may include a wireline interface with transmitters, receivers, and/or transceivers to support communication such as/using Ethernet, High-Definition Multimedia Interface (HDMI), Universal Serial Bus (USB), or coaxial cables. Network module 206 may also include a wireless interface with transmitters, receivers, and/or transceivers to support communication such as/using Bluetooth, GPS, or Wi-Fi. Other forms of physical layer interfaces and communication protocols may be used over Network module 206.

Power system 208 may include one or more batteries and/or one or more external power interfaces to provide electrical power to computing device 200. Each battery of the one or more batteries can be electrically coupled to the computing device 200 and provide stored electrical power. In some cases, the batteries may be configured to be removable and portable. In some embodiments, the batteries may be configured to be internal to the computing device 200. In some cases, the batteries may be rechargeable via an external power interface. In other examples, the batteries can be non-rechargeable batteries.

I/O module 208 may be configured to send data to/receive data from users and devices interacting with computing device 200. For example, I/O module 208 may configured to receive data from one or more input devices, such as a keyboard, a mouse, a touch screen, a track ball, a joystick, or other similar devices. Similarly, I/O module 208 may be configured to send data to one or more output devices, such as screens, speakers, printers, light emitting diodes (LEDs), or other similar devices.

The computing device 200 can take various forms, such as a web server, a database server, a desktop computer, a laptop, and/or a mobile device.

B. Example Computer Network

Figure 3:
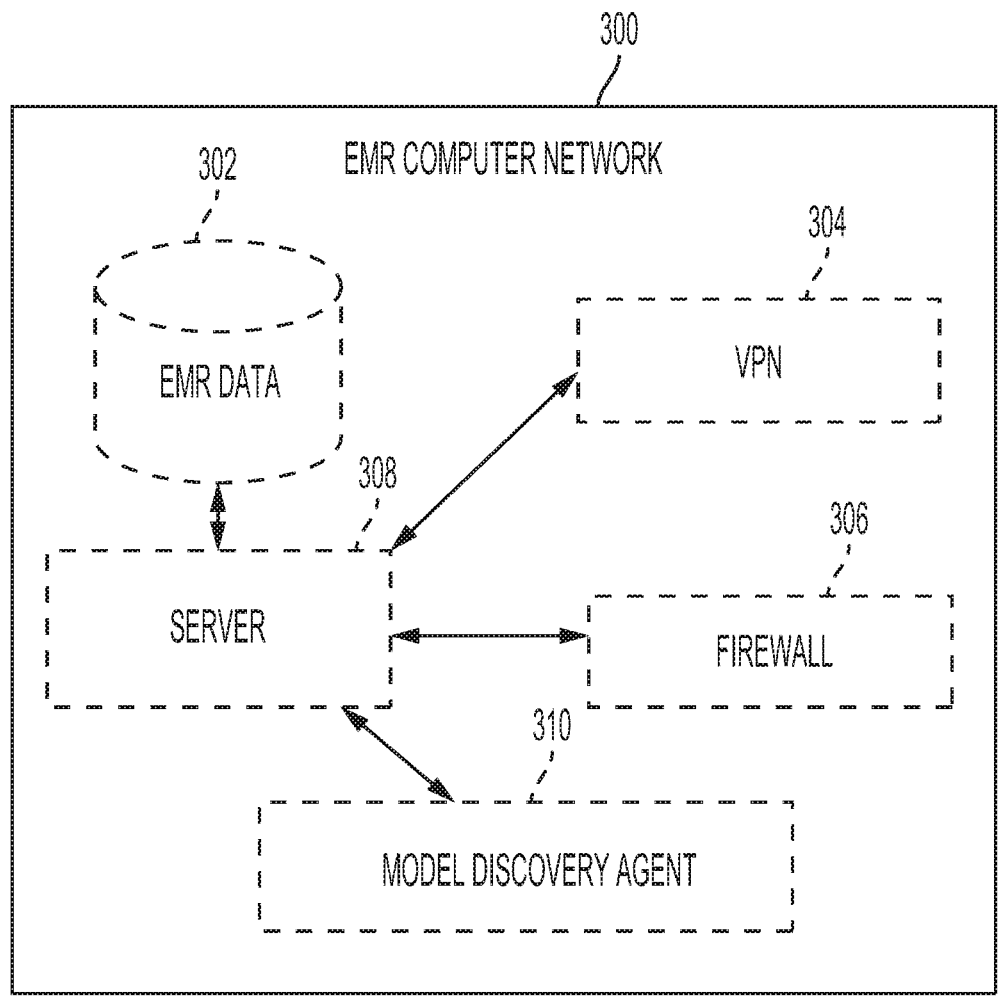
FIG. 3 depicts a simplified block diagram of an example EHR computer network, in accordance with example embodiments.

FIG. 3 is a simplified block diagram of an example EHR computer network 300, in accordance with the example embodiments. EHR computer network 300 may be a computing system hosted by a health data provider, such as a large medical institution (e.g. hospital, university research center, physician group, etc.), a health information exchange (HIE), and/or a health data vendor/aggregator. In some embodiments, EHR computer network 300 may be a cloud-based computing system used by the health data provider. In some embodiments, EHR computer network 300 may be a computing system hosted on computing devices located at the health data provider facilities.

EHR computer network 300 may include, for example, EHR data storage 302, server 304, virtual private network (VPN) 306, firewall 308, and/or model discovery agent 310. Each component on EHR computer network 300 may be embodied by one or more computing devices 200.

EHR data storage 302 may be a database server used to store sensitive EHRs of a population related to the functions of the health data provider. For example, the EHRs of a health data provider representing a hospital may contain patient records of patients who have accessed healthcare treatment at the particular hospital in the last 30 years. In the example embodiments, EHR data storage 302 contains sensitive PHI data not authorized for public release. Consequently, EHR data storage 302 may be configured to implement access control, user authentication, and/or data encryption. In example embodiments, actual EHR storage 106 may be embodied by EHR data storage 302.

To add additional security measures for PHI data, EHR computer network 300 may include VPN gateway 304 and firewall 306, which can be one or more specialized routers or server devices that protect EHR computer network 300 from unauthorized access to the devices, applications, and component therein. Firewall 306 may be configured to allow access from authorized users and to deny access to unauthorized users. Firewall 306 may also provide filtering, intrusion detection, virus scanning, and/or other network security services. VPN gateway 304 may allow EHR computer network 300 to extend network access to remote users on public networks through the use of gateway. VPN gateway 304 may be configured for connection by way of tunneling protocols, such as Internet Protocol Security (IPSEC), or traffic encryption.

Server 308 may represent one or more servers on EHR computer network 300 that are configured to provide various functionalities or services to the other components on the network. For example, server 308 may be a web server configured to, in response to a request from a client, retrieve data from EHR data storage 302 and provide the data to the client in the form of a graphical user interface (GUI). In another example, server 308 may be an application server.

Model discovery agent 310 may be configured to interact with the various components of EHR computer network 300. In accordance with the example embodiments, model discovery agent 310 may be embodied by at least the components of model discovery agent 104 to facilitate synthetic EHR generation on EHR computer network 300.

EHR computer network 300 may contain additional components to those described above (e.g.: load balancers, proxy servers, etc.). In addition, various client devices, such as personal computers or mobile device may be connected to EHR computer network 300 at any given time. Any component on EHR computer network 300 may be replicated across multiple computer devices to provide data duplication and increase capacity of services. Replicated components may be located at various computing locations to ensure high availability in case of power failure at one computing location. In some cases, EHR computer network 300 may consist of a few devices and a small number of components. In other deployments, EHR computer network 300 may span across multiple physical locations and hundreds of devices and components.

In some embodiments, the components of EHR computer network 300 may be administered, owned, or associated with different entities. For example, model discovery agent 310 may be associated with a synthetic EHR aggregation system configured to provide synthetic EHR to third party users, while the remaining components could be associated with a health data provider, such as a hospital. In the example scenario, model discovery agent 310 may be deployed onto EHR computer network 300 by a synthetic EHR aggregation system to generate synthetic EHR containing no PHI data based on the protected PHI information hosted on EHR data storage 302. Upon certifying that the synthetic EHR data produced by model discovery agent 310 is representative of the data on EHR data storage 302, one or more learned representative models from model discovery agent 310 may be transmitted to a central repository hosted by the synthetic EHR aggregation system. These representative models may be referred to as discovered models.

Figure 4:
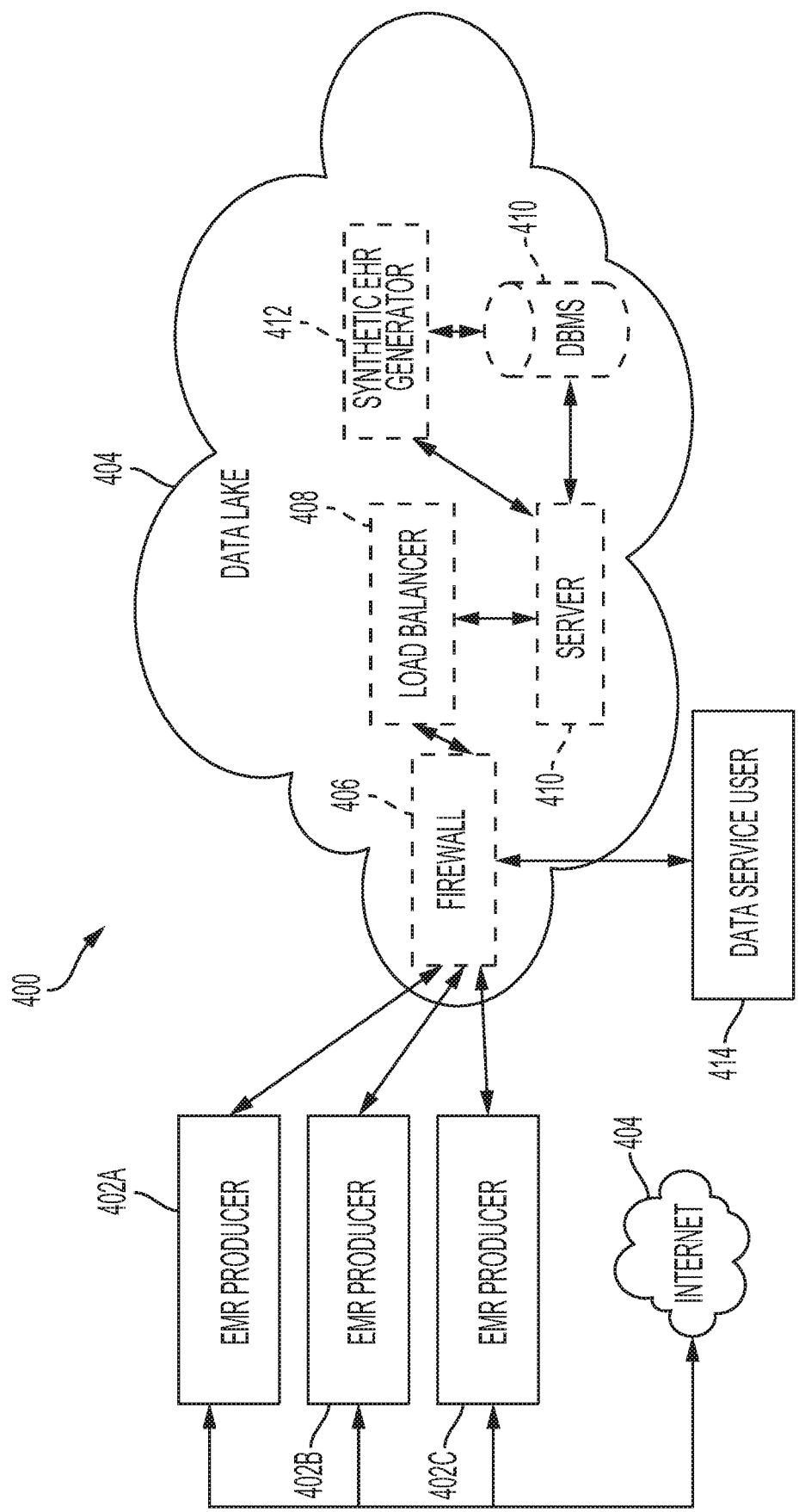
FIG. 4 depicts a simplified block diagram of an example synthetic EHR aggregation system that uses one or more EHR computer networks, in accordance with example embodiments.

FIG. 4 is a simplified block diagram of an example synthetic EHR aggregation system 400 utilizing one or more EHR computer networks 300, in accordance with the example embodiments. Synthetic EHR aggregation system 400 includes one or more EHR producers 402, data lake 404, and a data service user 414.

As stated above with respect to FIG. 3, EHR producers 402 may represent health data providers, such as a large medical institutions, HIEs, or health data vendors. In synthetic EHR aggregation system 400, each EHR producer 402 may be embodied by EHR computer network 300 that communicates with data lake 404 via firewall 406. Each EHR producer 402 may transmit one or more discovered models to data lake 404 or may receive instructions from data lake 404 to perform certain actions, such as updating software on model discovery agent 310. In some embodiments, EHR producers 402 may be connected to Internet 418 to facilitate access to public data via HTTP requests or other inter-network communication protocols. EHR producers 402 may use this public data as input to their respective model discovery agents, as discussed above.

Data lake 404 may include one or more data centers configured to aggregate discovered models from one or more EHR producers 402, produce synthetic EHR data using the discovered models, and distribute the synthetic EHR data to data service users 414. All devices in data lake 404 may be embodied by one or more computing devices 200.

Load balancer 408 may distribute traffic among one or more physical or virtual devices that host server 410. For instance, if server 410 includes multiple physical or virtual computing devices, load balancer 408 may distribute network traffic and computational tasks across the multiple computing devices so that no one computing device is processing more tasks than the others (or more than its specified capabilities allow).

Server 410 may include one or more web servers that host web applications that utilize synthetic EHR data from DMBS 410. These web applications may provide analytics capabilities for data service user 414. For example, web applications may include GUIs for viewing, filtering, and interacting with synthetic EHR data.

DBMS 410 represents a database management system configured to aggregate and store discovered models gathered from each EHR producer 402 and store generated synthetic EHR data from synthetic EHR generator 412. Accordingly, DBMS 410 may include multiple database technologies, including, but not limited to, graph databases, document databases, and column store databases. DBMS 410 may be a single database or may be a distributed database hosted across many separate devices. In some embodiments, additional load balancers may be used to distribute traffic amongst database devices. DBMS 410 may also provide administration utilities, such as defragmentation and analysis.

Synthetic EHR generator 412 may include one or more processes to generate synthetic EHR data. This may include obtaining one or more discovered models from DBMS 410, simulating the one or more discovered models to produce synthetic EHR data, and returning the synthetic EHR data back to DBMS 410 for storage. In some embodiments, synthetic EHR generator 412 may be configured to generate new synthetic EHR data any time a discovered model is added/updated by EMR producers 402. Such an addition/update may be referred to as new version of the discovered model. As such, synthetic EHR generator 412 may be designed to associate a version index with each set of generated synthetic EHR data. This version index may detail the specific versions of discovered models that were used to generate each set of synthetic EHR data.

Data service user 414 may, for example, be a large medical research institution or hospital system. Data service user 414 may access the capabilities of data lake 404 via firewall 412. In some instances, access to data lake 404 may be on a subscription basis. For example, access to basic features of data lake 404 may be available to the public while more advanced features may be limited to subscribers.

C. Synthetic Life

In accordance with embodiments described herein, a synthetic life may refer to a representation of health related events that contribute to the medical history of a synthetic person over the course of a simulated lifetime. A synthetic life may be divided into separate time steps, each step representing a fixed time increment of the synthetic life. For example, time increments may be decades, months, years, weeks, days, or another time increment.

Time steps in the synthetic life may include one or more health related events, such as disease treatments, infections, hospital visits, immunizations, medication subscriptions, or other healthcare treatments. Health related events may be stored as immutable data objects and may be outputted as synthetic EHR data reflecting the synthetic life.

For a given time step, a health related event may occur with an associated probability based in part on health attributes of the particular synthetic life. Example health attributes may include age, weight, income, and/or diet. These health attributes may be stored as mutable data objects that are associated with the particular synthetic life. Health attributes may change based on the health related events that occur during a synthetic life. For example, a diabetes diagnosis may directly affect the weight attribute of a synthetic life.

In some embodiments, a synthetic life may track calendar dates for each time step and update these calendar dates as the synthetic life progresses over time. This may allow real life events to directly affect the time steps in the synthetic life. For example, a time step in a synthetic life may occur on a calendar date where a new drug is brought to market. Thus, time steps occurring on or after that calendar date may be able to utilize the new drug to treat the synthetic person. In other cases, a time step in a synthetic life may occur on a calendar date that had a prevalent flu season. This may increase the chance that the synthetic person contracts the flu during that time step.

Figure 5:
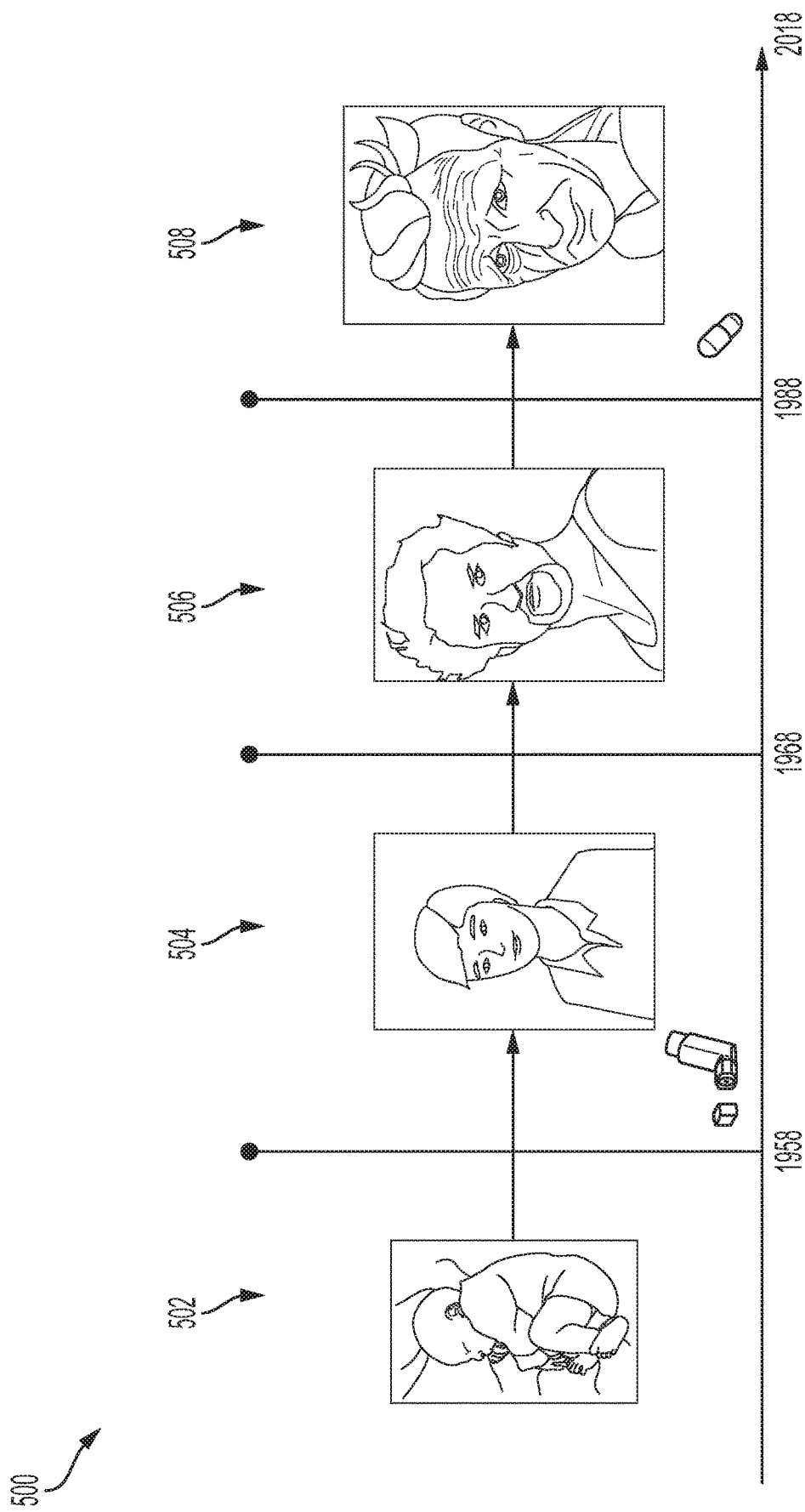
FIG. 5 illustrates a synthetic life, in accordance with example embodiments.

FIG. 5 illustrates an example synthetic life 500, in accordance with example embodiments. For purposes of example, synthetic life 500 may be divided into four "life stages", each containing multiple time steps.

Stage 502 may represent a synthetic birth of a synthetic person, where the calendar year is set to 1958. In stage 502, the synthetic person may be diagnosed with a severe form of asthma, a high risk for diabetes, and a high risk for rheumatoid arthritis. These pieces of health information may be stored as mutable health attributes of the synthetic person for use in later life stages and/or time steps.

Stage 504 may represent the synthetic life during the 10 years after stage 502. At the end of stage 504, the synthetic person is 10 years old and the calendar year is 1968. In stage 504, the asthma developed in stage 502 may be treated by an inhaler, which was introduced around the real year 1965. Accordingly, the severe asthma of stage 502 is treated in stage 504. Such treatments may be recorded as immutable health related events that are outputted as synthetic EHR data. Additionally, health attributes of the synthetic person may be modified by such treatments to reflect that asthma may not be a critical health concern in future stages and/or steps. On the contrary, if the synthetic person had been born in the calendar year of 1900, asthma inhalers would not have existed and asthma may have remained a critical health concern in future stages and/or time steps of the synthetic life.

Stage 506 may represent the synthetic life during the 20 years after stage 504. At the end of stage 506, the synthetic person is 30 years old and the calendar year is 1988. In stage 506, the high risks of diabetes and rheumatoid arthritis of stage 502 may start to surface. The diabetes may create a higher risk of heart attack and stroke, and the fatigue from rheumatoid arthritis may reduce healthcare facility visits. Once again, these health factors may be recorded as health related events that are outputted as synthetic EHR data and the health attributes of the synthetic person may be changed to reflect the events.

Stage 510 may, for example, represent the synthetic life 30 years after stage 506. At the end of stage 510, the synthetic person is 60 years old and the real year is 2018. In stage 510, the rheumatoid arthritis may be fully treated by the introduction of adalimumab in the early 2000's. Furthermore, the synthetic person may introduce new lifestyle habits to keep the diabetes under management.

Synthetic life 500 is presented for the purpose of example. In some embodiments, a synthetic life may span across thousands of life stages and/or time steps, for example, each containing hundreds (or more or less) of health related events that are outputted as synthetic EHR data. Each synthetic life may be simulated based on health attributes and real life medical treatments that may occur at a different calendar dates of the synthetic life.

Moreover, each synthetic life may span over a calculated life duration. This duration may be randomly generated for each synthetic life or may be based on health attributes of the synthetic person. Accordingly, a synthetic life may be configured to initiate at a randomly generated calendar date and continue simulation until the end of the calculated life duration (which may be referred to as synthetic death). In some embodiments, randomly generated calendar dates may be a range of calendar dates from a predefined past date (e.g. Jan. 1, 1900) to the current date.

In example embodiments, model discovery agent 310 and/or synthetic EHR generator 412 may utilize one or more state machines to simulate health related events across one or more synthetic lives. In particular, one or more state machines may be configured to track health related events and output synthetic EHR data relating to the one or more simulated synthetic lives.

Figure 6:
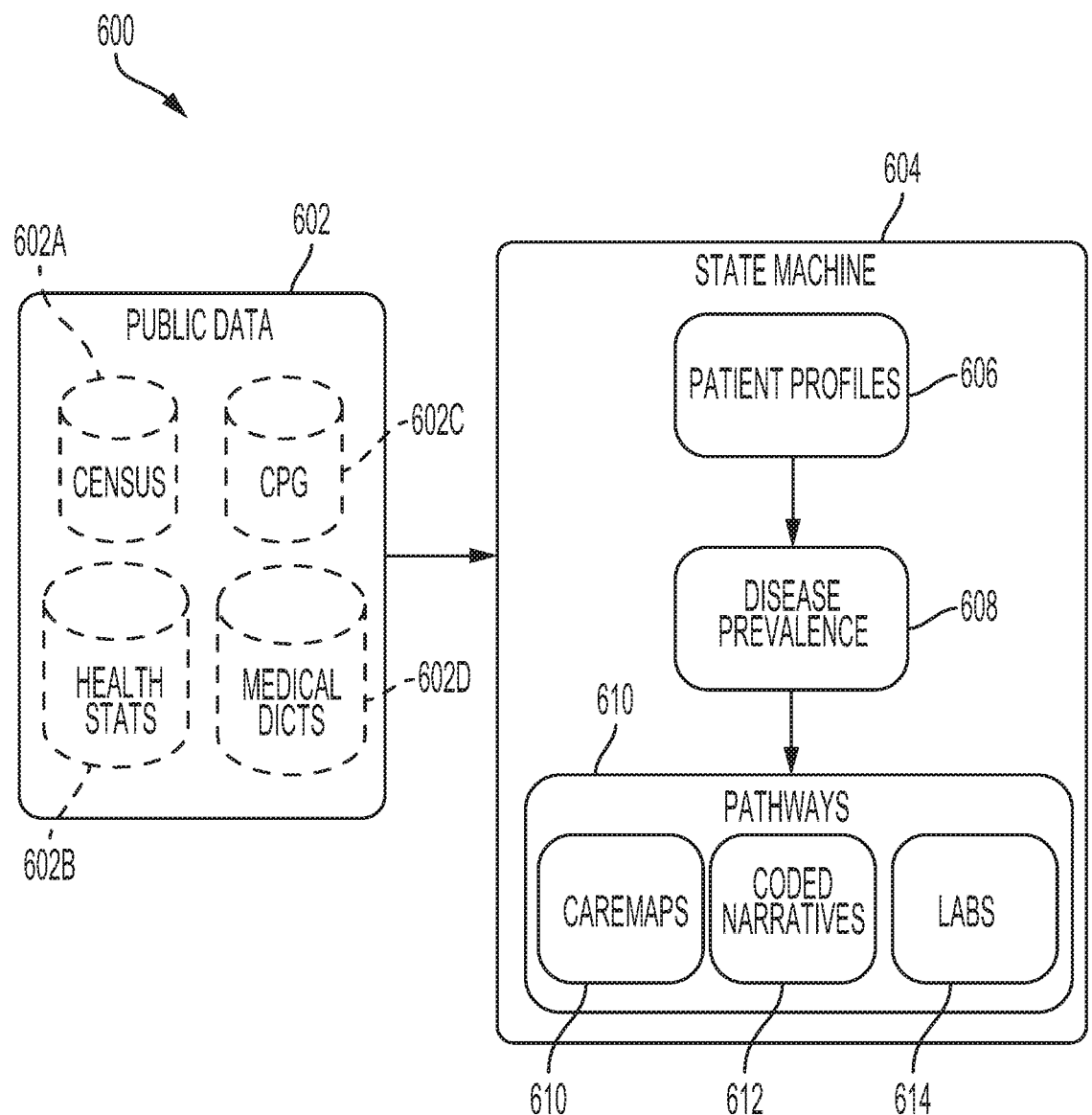
FIG. 6 depicts an example configuration framework for configuring a state machine, in accordance with example embodiments.

FIG. 6 illustrates an example configuration framework 600 for configuring a state machine to generate synthetic EHR data for one or more synthetic lives. Configuration framework 600 may include public data source 602 and state machine 604. In example embodiments, public data 102 may take the form of public data source 602 and state machine 104A may take the form of state machine 604.

Public data source 602 may include census data 602A or similar demographic information, health incident statistics 602B, clinical practice guidelines (CPGs) 602C or similar diagnostic and treatment protocols, and medical coding dictionaries 602D. These data sources may be a collection of separate data sources hosted by different public data providers or may be an aggregated data source hosted by a single public data provider or some other entity.

Census data 602A may include information on health insurance rates, fertility rates, disabilities rates, and/or other socioeconomic indicators within a geographic region. For example, census data 602A may contain information on how many middle income individuals without health insurance live in city.

Health incident statistics 602B may include regional information related to the prevalence of one or more diseases occurring in a population of interest and the medical procedures and/or medications that have been administered to/performed on patients contracting the diseases. For example, health incident statistics 602B may contain information about rate of HIV contraction and rate of HIV medication distribution in a given city.

CPGs 602C may include outlines of appropriate treatment protocols for specific diseases and health problems. Protocols may include a known series of clinical steps to be performed to achieve a specific patient outcome. For example, CPGs 602C may outline the operating procedure for how to treat a case of lupus as it progresses in severity.

Medical coding dictionaries 602D may include records of standard medical terminologies. Since coded data is used extensively in EHRs to detail patient health, state machine 604 may use medical coding dictionaries 602D to output synthetic EHRs in a similar format to actual EHRs for easy use by medical researchers. Furthermore, medical coding dictionaries 602D may be used to decode and match CPGs that use similar medical terminologies Components of public data source 602 may be utilized to configure state machine 604. This may include configuring patient profiles 608, disease prevalence 608, pathways 610.

Patient profiles 606 may include data defining a population of interest. For example, patient profiles 606 may utilize census data 602A to determine population information corresponding to a geographic area serviced by a particular health data provider. This information may be utilized by state machine 604 to initialize a synthetic population corresponding to the same geographic area.

Disease prevalence 608 may include statistics on the prevalence of various diseases for a given population. For example, disease prevalence 608 may utilize census data 602A and health incident statistics 602B to determine likelihoods for developing specific health conditions. Such information may include the likelihood for a woman living in Michigan under the age of 40 to develop breast cancer or the likelihood for a child living in California to develop asthma. Accordingly, state machine 604 may utilize disease prevalence 608 to determine whether a synthetic person will develop a specific health/disease condition over the course of a synthetic life.

Pathways 610 may include known sequences of health related events associated with various health/disease conditions. State machine 604 may utilize pathways 610 to simulate the health related events that may results from a specific health condition. To represent these health relate events, pathways 610 may include caremaps 610A, coded narratives 610B, and labs 610C.

Caremaps 610A may provide sequences of encounters that a patient experiences when visiting a medical facility.

For example, caremaps 610A utilize CPGs 602C to describe an encounter sequence for visiting an Emergency Room (ER). This sequence may include a discussion with a triage nurse, admission to the ER, and visitation by an ER doctor.

Coded narratives 610B may provide medications regimens that patients should follow to treat a given disease. For example, coded narratives 610B may utilize CPGs 602C to describe a medication regimen treating bipolar disorder. This regimen may include taking a 100 mg doses of medication every morning for 3 weeks.

Labs 610C may provide procedures that medical facilities utilize for processing patient health information. For example, labs 610C may utilize CPGs 602C to describe procedures for processing patient glucose readings. This procedure may include details on false positive rates and how information is reported back to medical professionals for treatment.

Caremaps 610A, coded narratives 610B, and labs 610C are just example elements of pathways 610. In some embodiments, pathways 610 may contain hundreds or thousands of elements that each relate to distinct parts of a disease/health condition. Moreover, one or more knowledge models may be utilized to update pathways 610 and/or state machine 604 in accordance with the embodiments herein.

Notably, the configuration framework 600 is just an example of how state machine 604 can be arranged. Other configurations are possible.

C. Example State Transition Machine

Figure 7:
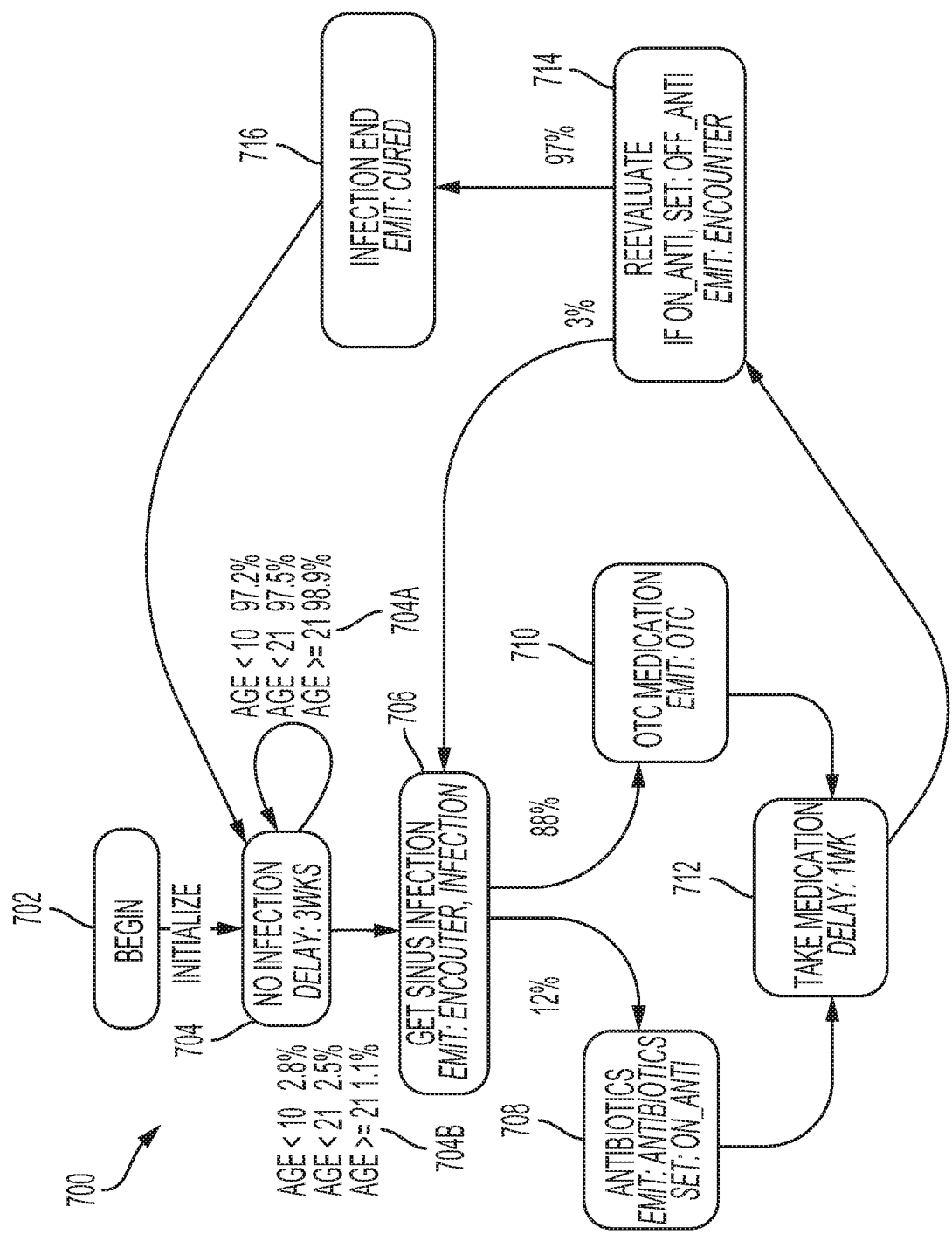
FIG. 7 depicts an example state machine configured to generate synthetic EHR, in accordance with example embodiments.

FIG. 7 illustrates a state machine 700 representing a clinical pathway for a sinus infection, in accordance with the example embodiments. State machine 700 may represent one state machine of a plurality of state machines that may be configured via configuration framework 600 to generate synthetic EHR data from one or more synthetic lives.

State machine 700 demonstrates several different types of states representing health related events associated with a sinus infection. Accordingly, a transition to a next state from a current state in state machine 700 may depend on the current health related event and the health attributes of the synthetic person. In an event that a current state has multiple next states, transitions may occur with an associated probability. For example, transitions out of state 706 may indicate probabilities that specific treatments will be administered. Such probabilities may be determined by configuration framework 600, based on disease prevalence 608 and pathways 610, for example. In some embodiments, the current calendar date of the synthetic life may be tracked and utilized to determine transition probabilities.

State machine 700 may start at initialization state 702. At state 702, state machine 700 may read a configuration file specifying properties such as medical terminology codes used in diagnosis, the attributes of the synthetic person modeled by state machine 700, transitions probabilities to other states, and/or other properties.

After initialization, state machine 700 may transition to state 704. State 704 may represent a no-infection health condition. While in state 704, the state machine 700 may be configured to delay action for 3 weeks by remaining in state 704. This delayed action may reflect a real life delay for symptoms of a corresponding disease to surface. This delay may allow state machine 700 to derive the correct amount of time between states. In some embodiments, the delay action may be represented by a dummy state in state machine 700.

In the example embodiments, state 704 contains two types of transitions: self-transitions 704A, which may reflect that the health condition of the synthetic person has not changed, and next state transitions 704B, which may reflect that the health condition of the synthetic person has changed. Self-transition 704A and next state transitions 704B may be configured with one or more probability groups determined from real life medical scenarios. For example, sinus infections are known to be prevalent among younger individuals. This may be reflected by younger age groups having a higher probability of transitioning to an infection state 706.

Accordingly, state machine 700 may utilize one or more health attributes of a synthetic life to select a probability group. For example, the age attribute of a synthetic life may be utilized to determine the correct probability group (e.g. younger than 10, between 10 and 21, older than 21) for self-transition 704A and next state transition 704B. Subsequently, state machine 700 may utilize a random number generator to select a given transition within the probability group. For example, state machine 700 may generate a random number between 0 and 1 (e.g. 0.77), associate the generated number with a specific transition within a probability group (e.g. age <21, [0 −0.975]), and select the specific transition. In some embodiments, the random number generator may be seeded with a predefined seed stored by state machine 700. This predefined seed may allow state machine 700 to generate a consistent output given the same seed and transition probabilities.

In state 706, a sinus infection health event may occur. When entering a new state, state machine 700 may be configured to emit health events related to the new state, timestamp the health events, and record the health events into the output synthetic EHRs. For example, state 706 may include a health event describing an encounter with a health care professional and an indication of a sinus infection. Transitions probabilities out of state 706 to state 708 or state 710 may reflect typical treatments for a sinus infection: over-the-counter (OTC) medications or antibiotics. As described above, state machine 700 may utilize a random number generator to select a given transition from the probabilities.

In state 708, antibiotics may be prescribed. An antibiotic health event may be emitted to indicate that antibiotics were prescribed to treat the infection. In addition, a health attribute may be set to indicate that antibiotics are currently prescribed to the synthetic person. In some embodiments, this health attribute may be accessible to other state machines/clinical pathways to inform them not to administer additional antibiotics during their own implementation. For example, if antibiotics are prescribed for a sinus infection, they may not be prescribed if a person develops an eye infection at the same time. In state 710, over-the-counter medication is prescribed. An OTC flag may be emitted to the output synthetic EHRs indicating that OTC medications were prescribed to treat the sinus infection. Note that state 708 and state 710 are mutually exclusive. This simulates the concept that two treatments are never simultaneously prescribed to a patient for a sinus infection.

In state 712, the medication prescribed in either state 708 or state 710 may be taken and a one-week delay action is set. This delay action may indicate a treatment period of the medication.

In state 714, a reevaluation may be administered to indicate whether medications from states 708 or 710 succeeded in curing the sinus infection. In state 714, state machine 700 may emit a health related event indicating a second visit to a health care professional. Additionally, state 714 may include an antibiotic check. If the antibiotics health attribute is set to be "true" from state 708, then state 714 may set the antibiotic health attribute to be "false" to indicate that antibiotics are no longer being prescribed. Transition probabilities out of state 714 to state 716 or state 706 may reflect the typical success rates for sinus infection treatment. For example, while most people are cured, a small percentage may not be cured either from the severity of the infection or from not complying with the medication regiment. This small percentage is represented with a transition back to state 706. As described above, state machine 700 may utilize a random number generator to select a given transition from the probabilities.

In state 716, the sinus infection is cured. State machine 700 may emit a health related event indicating that the sinus infection is cured. State machine 700 may transition back into state 704 to indicate that no infection is present.

State machine 700 is presented for the purpose of example. Health related events, transitions, delays, emits, attributes and/or any of the components of state machine 700 as described above may be combined in various orders and arrangements to create clinical pathways and/or state machines corresponding to different health/disease conditions. Model discovery agent 310 and/or synthetic EHR generator 412 may combine a plurality of separate clinical pathways and/or state machines describing different health/disease conditions to generate synthetic EHR data for one or more synthetic lives.

FIG. 8 depicts example output synthetic EHR 800 that may be generated from state machine 700, in accordance with example embodiments. Synthetic EHR 800 may be formatted as JavaScript Object Notation (JSON) in a Fast Healthcare Interoperability Resources (FHIR) data standard. In some embodiments, EHR 800 may be formatted in CSV, TSV, XML, or may be stored directly to a relational database management system (RDBMS).

In some embodiments, synthetic EHR 800 may be classified with a resource 802. In accordance with the embodiments herein, a resource may be defined as an entity that has a known identity that can be addressed, identifies itself as a single type in a collection of resource types, and contains a set of structured data items as described by the definition of the resource type. Resource types may include, but are not limited to, condition (representing a clinical condition, problem, diagnosis, or other clinical concept that is of concern), account (representing financial charges to a patient or hospital), and patient (demographics and other administrative information about an individual receiving care). Resource types may be used to organize the generated EHRs into known features. For instance, a "condition" type may have features such as clinical status, verification status, and subject (indicating a patient who is associated with the condition record).

Synthetic EHR 800 may include, for example, unique identifier 804 in order for other EHRs to reference synthetic EHR 800. In some embodiments, the unique identifier 804 is a universally unique identifier (UUID).

Synthetic EHR 800 may include, for example, coding references 806 used by the resource. For example, coding reference 806 may display a particular medical coding dictionary, a medical code of the medical coding dictionary, and the related medical term used by the resource.

Synthetic EHR 800 may include, for example, reference statements 808. Reference statements 808 may use the unique identifiers of other EHRs to obtain the specified information instead of directly listing a subject or context.

Synthetic EHR 800 may include timing information 810. Timing information 810 may provide information on when synthetic EHR 800 was created during the timeline of a synthetic life.

Synthetic EHR 800 may be embodied by any resource types, each of which may contain may contain additional features, such as insurance information, addresses, dates of birth, to describe healthcare scenarios.

Notably, the output synthetic EHR 800 of FIG. 8 is just an example of how synthetic EHR data generated from a state machine can be arranged. Other arrangements are possible.

D. Example Model Tuning

Figure 9:
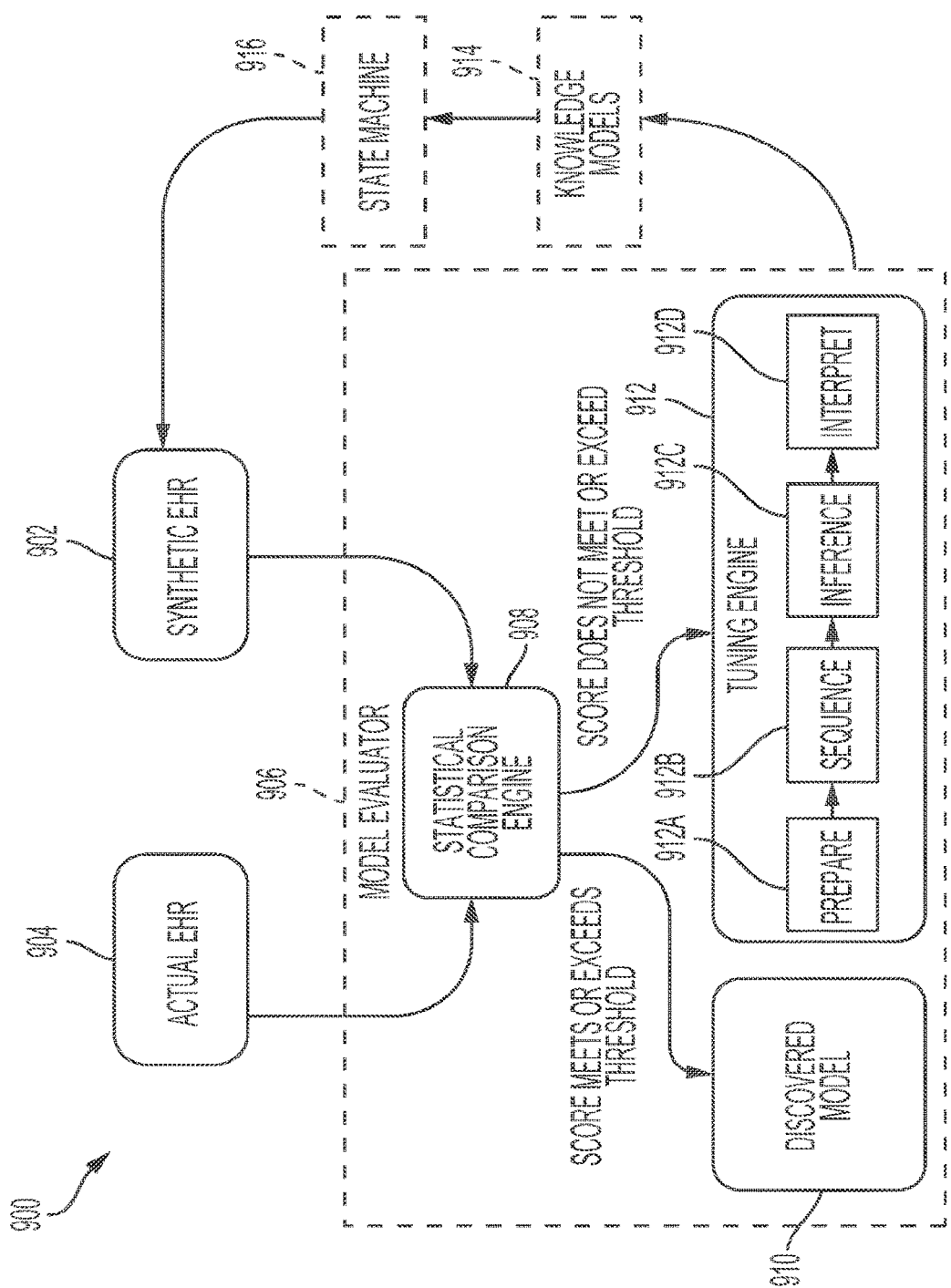
FIG. 9 depicts an example model tuning process for determining representative synthetic EHR data, in accordance with example embodiments

FIG. 9 illustrates an example model tuning process 900 for determining representative synthetic EHR data, in accordance with the example embodiments. Model tuning process 900 may include synthetic EHR 902, actual EHR data 904, model evaluator 906, knowledge models 914, and state machine 916. In example embodiments, model evaluator 104D may take the form of model evaluator 906, knowledge models 104B may take the form of knowledge models 914, and state machine 104A may take the form of state machine 916.

Synthetic EHR data 902 may represent synthetic EHR data generated from state machine 916 to represent a population of interest. Actual EHR data 904 may represent actual EHR data recorded from the same population of interest. Both synthetic EHR data 902 and actual EHR data 904 are fed into statistical comparison engine 908, which may be configured as a component of model evaluator 906. The output of statistical comparison 906 may then be scored and used to decide whether to output discovered model 910 or apply tuning engine 912 to update synthetic EHR data 902. Model tuning process 900 may be run multiple times to improve representativeness of the synthetic EHR data.

Statistical comparison engine 908 may include, for example, a series of statistical tests for comparing the distribution of data in both the synthetic EHR data 902 and actual EHR data 904, and generating a single similarity score to represent the congruency of the datasets. Statistical comparison engine 908 may include configuration methods to indicate features of synthetic EHR data 902 that are directly correlated with features in actual EHR data 904 (e.g. using one or more dictionaries). For example, synthetic EHR data 902 may label a feature describing the age of a person as "age" while the actual EHR data may label the same feature as "years".

Statistical comparison engine 908 may be configured to preprocess the EHR data by grouping values of numerical feature (e.g. age) into a smaller number of bins. Bins may be predetermined or calculated based on range of the numerical elements. Categorical features (e.g. race) may be one hot encoded into binary representations.

Statistical comparison engine 908 may be configured to apply a univariate scoring test between the distributions of a similar feature in synthetic EHR data 902 and actual EHRs 904. The univariate scoring test may include a chi-squared test, Kolmogorov-Smirnov test, area under curve (AUC), and/or similar statistical comparison tests. In some embodiments, multiple scoring tests may be run and averaged to create a univariate score for each feature. In other embodiments, multiple scoring tests may be run and one scoring test of the multiple is chosen to create a univariate score for each feature.

Statistical comparison engine 908 may be configured to combine the univariate scores from one or more features into a single output score, the combination based on a predetermined weighting scheme. For example, the univariate analysis score of an "age" feature may be combined with the univariate analysis score of an "income" feature. Accordingly, each univariate analysis may be added and/or removed depending on the synthetic EHR data/actual EHR data being compared. For example, removing a specific univariate analysis from the single output score calculation may involve setting the weight of the specific univariate analysis to zero. In some embodiments, a multivariate analysis of features may be used instead of or in addition to the weighted combination of multiple univariate analysis of features.

After generating a single output score, statistical comparison engine 908 may compare the single output score to a predefined threshold score. If the single output score meets or exceeds the threshold score, model tuning process 900 may indicate that synthetic EHR data 902 is representative of actual EHR data 904. This may result in model tuning process 900 outputting discovered model 910. As described above, discovered model 910 may be transmitted to a synthetic EHR aggregation system to facilitate generating representative synthetic EHR data.

If the single output score does not meet or exceed the threshold score, model tuning process 900 may indicate that synthetic EHR data 902 is not representative of actual EHR data 904. This may result in model tuning process 900 requesting tuning engine 912 to update knowledge models 914. In example embodiments, tuning engine 912 may utilize prepare phase 912A, sequence phase 912B, inference phase 912C, and interpret phase 912D to update knowledge models 914. In turn, knowledge models 914 may reconfigure one or more clinical pathways of state machine 916 to generate more representative synthetic EHR data, in accordance to the embodiments described herein.

Prepare phase 912A may include extracting source data based on predetermined configuration parameters of tuning engine 912. This extraction may include mapping actual EHR data 904 to align health related events with those used by clinical pathways in state machine 916. For example, actual EHR data 904 may label a feature describing the condition of a person as "health condition" while the state machine 916 may be configured to read same feature as "health state". Thus, mapping may enable tuning engine 912 to resolve different data codification systems that health data providers may use. Extracted health related events may utilized by tuning engine 912 as parameters to infer probabilities of health related events in one or more clinical pathways. Consequently, extracted features may be referred to as inference parameters (i.e. variables describing priors and likelihoods).

Sequence phase 912B may include representing known clinical pathways (i.e. from current clinical pathways from state machine 916) in a probabilistic graphical model format. Such a graphical representation may be in the form of a Bayesian network stored in one or more graph databases deposed in model evaluator 906 and may utilize inference parameters as evidence variables (e.g. observed variables). In some embodiments, Sequence phase 912B may add health related events found in actual EHR 904 and/or may adjust the number of transitions between health related events.

Inference phase 912C may include determining one or more distribution probabilities for transitions between health related events in the graphical representation. For example, inference phase 912C may infer the probability a particular patient makes a single transition within the graph based correlation on specified inference parameters. This inference may utilize probabilistic inference methods on a Bayesian network to compute posterior distributions of variables given evidence variables. In some embodiments, inference phase 912C may prune low probabilities within the distribution of probabilities, for example, to prevent the graphical representation from overfitting.

Interpret phase 912D may include selecting an inference method and transforming the graphical representation into a digestible form. Selecting an inference method may be performed by selecting a distribution probability based on the validity of pruning metrics and interpreting the model for synthetic data generation from the inferred graph. Transforming may include representing the inferred graph as a JSON file. Accordingly, interpret phase 912D may output one or more updated clinical pathways that may be stored as knowledge models 914 (e.g. as a flat file or in a document database).

After the completion of interpret phase 912D, the knowledge models 914 may be provided to state machine 916 along with configuration parameters to demographics and population counts, (e.g. patient profiles 606 and disease prevalence 608). State machine 916 may proceed to simulate the specified population to generate synthetic EHR data 902. This data may again be compared to actual EHR data 904 via model tuning process 900. This cycle may repeat again and again until synthetic EHR data 902 is representative of actual EHR data 904.

Notably, the components of model tuning process 900 are just examples of how to adjust state machine 916 to generate more representative synthetic EHR data. Other arrangements of model tuning process 900 are possible.

III. Example Methods

Figure 10:
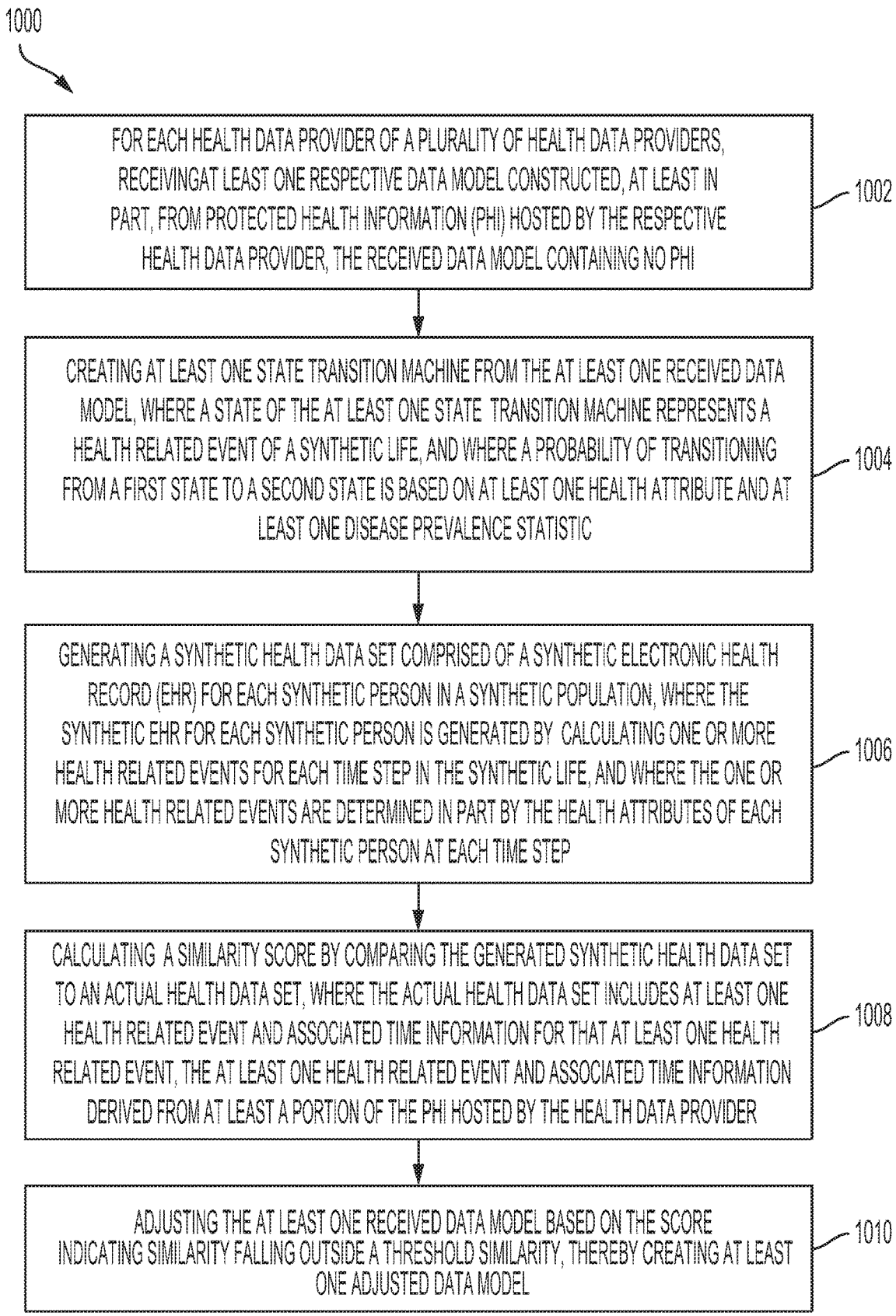
FIG. 10 depicts a flow chart illustrating an example method, in accordance with example embodiments.

FIG. 10 is a flow chart illustrating an example method 1000, in accordance with example embodiments.

At block 1002, the method 1000 can include for each health data provider of a plurality of health data providers, receiving at least one respective data model constructed, at least in part, from protected health information (PHI) hosted by the respective health data provider, the received data model containing no PHI. For example, receiving at least one respective data model constructed at least in part from data hosted by the respective health data provider may be done via a synthetic model discovery agent 310 as shown and described with reference to FIG. 3.

At block 1004, the method 1000 can include creating at least one state transition machine from the at least one received data model, where a state of the at least one state transition machine represents a health related event of a synthetic life, and where a probability of transitioning from a first state to a second state is based on at least one health attribute and at least one disease prevalence statistic. For example, the state transition machine may be configured as shown and described with reference to FIG. 6.

At block 1006, the method 1000 can include generating a synthetic health data set comprised of a synthetic electronic health record (EHR) for each synthetic person in a synthetic population, where the synthetic EHR for each synthetic person is generated by calculating one or more health related events for each time step in the synthetic life, and where the one or more health related events are determined in part by the health attributes of each synthetic person at each time step. For example, the synthetic EHR may be an output of a state transition machine as configured in FIG. 6 and may be arranged as shown and described with reference to FIG. 8.

At block 1008, the method 1000 can include calculating a similarity score by comparing the generated synthetic health data set to an actual health data set, where the actual health data set includes at least one health related event and associated time information for that at least one health related event, the at least one health related event and associated time information derived from at least a portion of the PHI hosted by the health data provider. For example, the similarity score may be generated through a statistical comparison engine 908 as shown and described with reference to FIG. 9.

At block 1010, the method 1000 can include, adjusting the at least one received data model based on the score indicating similarity falling outside a threshold similarity, thereby creating at least one adjusted data model. For example, the adjusted data model may be configured via model tuning process 900 as shown and described with reference to FIG. 9.

What is claimed is:

1. A computerized method, comprising:
    receiving, by a computing device, a data model constructed, at least in part, from protected health information (PHI) hosted by a corresponding health data provider, the received data model containing no PHI, wherein the data model includes clinical pathways representing sequences of health related events;
    creating, by the computing device, a state transition machine from the received data model, wherein a state of the state transition machine represents a health related event of a synthetic life, and wherein a probability of transitioning from a first state to a second state is based on a health attribute and a disease prevalence statistic;
    generating, by the computing device, a synthetic health data set comprised of a synthetic electronic health record (EHR) for each synthetic person in a synthetic population, wherein the synthetic EHR for each synthetic person is generated by calculating health related events for each time step in the synthetic life, and wherein the health related events are determined in part by the health attributes of each synthetic person at each time step;
    calculating, by the computing device, a similarity score by comparing the generated synthetic health data set to an actual health data set including an actual EHR, wherein the actual health data set includes a health related event and associated time information for the health related event, where the health related event and associated time information are derived from the PHI hosted by the health data provider; and
    tuning, by the computing device, the received data model based on the score indicating similarity falling below a threshold similarity, thereby creating a tuned model by:
        representing the received data model as a probabilistic graphical model;
        determining probabilities of probabilistic graphical model based on the health related event from the actual health data set to infer a probability that a particular synthetic life will transition within the graph; and
        selecting a distribution probability based on interpreting the data model from the inferred graphical model probability to create updated clinical pathways in the tuned data model for use in the state transition machine.

2. The computerized method of claim 1, further comprising transmitting, to a second computing device, the received data model based on the score indicating similarity falling at or above the threshold similarity.

3. The computerized method of claim 2, wherein the second computing device is configured to aggregate received data models into an aggregate data model, and generate a synthetic health data set using the aggregate data model.

4. The computerized method of claim 1, wherein calculating the similarity score comprises applying a predetermined weighting scheme to a plurality of univariate analysis of the synthetic health data set and the actual health data.

5. The computerized method of claim 1, wherein creating the state transition machine includes supplementing the received data model with publicly available health information.

6. The computerized method of claim 1, wherein the probability of transitioning from the first state to the second state in the state transition machine is further based on a current calendar date of the synthetic life.

7. The computerized method of claim 1, wherein the transitions between states of the state transition machine comprise a probability the synthetic person will transition from a current health related event to a different health related event.

8. The computerized method of claim 1, wherein the synthetic life of the state transition machine begins at a randomly initiated first time within a predetermined range and ends at a second time, wherein the second time is based on a calculated life duration for the synthetic person.

9. The computerized method of claim 1, wherein determining probabilities of probabilistic graphical model further comprises pruning low probabilities to prevent the graphical model from overfitting.

10. The computerized method of claim 1, wherein tuning, by the computing device, the received data model based on the score indicating similarity falling below a threshold similarity, thereby creating a tuned data model further comprises mapping the actual EHR data to align health related events with those used by the clinical pathways in state machine to resolve conflicts in different data codification systems.

11. A computing system comprising:
    a health data repository constructed from protected health information (PHI) hosted by a health data provider;
    a computing device containing a received data model constructed from the health data repository, wherein the received data model contains no PHI and the data model includes clinical pathways representing sequences of health related events;
    a state transition machine that is (1) constructed from the received data model, wherein a state of the state transition machine represents a health related event of a synthetic life, wherein a probability of transitioning from a first state to a second state is based on a demographic, a health attribute, and a disease prevalence statistic, and (2) configured to generate a synthetic health data set comprised of a synthetic electronic health record (EHR) for each synthetic person in a synthetic population, wherein the synthetic EHR for each synthetic person is generated by calculating health related events for each time step in the synthetic life, wherein the health related events are determined in part by the health attributes of each synthetic person at each time step; and
    a processor configured to (1) calculate a similarity score by comparing the synthetic health data set to an actual health data set including an actual EHR, wherein the actual health data set includes a health related event and associated time information for the health related event, where the health related event and associated time information are derived from the PHI hosted by the health data provider, and (2) tune the received data model based on the score indicating similarity falling below a threshold similarity, thereby creating a tuned data model by:
  representing the received data model as a probabilistic graphical model;
  determining probabilities of probabilistic graphical model based on the health related event from the actual health data set to infer a probability that a particular synthetic life will transition within the graph; and
  selecting a distribution probability based on interpreting the data model from the inferred graphical model probability to create updated clinical pathways in the tuned data model for use in the state transition machine.

12. The computing system of claim 11, wherein the processor is further configured to transmit to a second computing device the received data model based on the score indicating similarity falling at or above the threshold similarity.

13. The computing system of claim 12, where the second server device is configured to aggregate received data models into an aggregate data model, and generate a synthetic health data set using the aggregate data model.

14. The computing system of claim 11, wherein calculating the similarity score comprises applying a predetermined weighting scheme to a plurality of univariate analysis of the synthetic health data set and the actual health data.

15. The computing system of claim 11, wherein the construction of the state transition machine includes supplementing the received data model with publicly available health information.

16. The computing system of claim 11, wherein the probability of transitioning from the first state to the second state in the state transition machine is further based on a current calendar date of the synthetic life.

17. The computing system of claim 11, wherein the transitions between states of the state transition machine comprise a probability the synthetic person will transition from a current health related event to a different health related event.

18. The computing system of claim 11, wherein determining probabilities of probabilistic graphical model further comprises pruning low probabilities to prevent the graphical model from overfitting.

19. The computing system of claim 11, wherein tuning the received data model based on the score indicating similarity falling below a threshold similarity, thereby creating a tuned data model further comprises mapping the actual EHR data to align health related events with those used by the clinical pathways in state machine to resolve conflicts in different data codification systems.

20. A non-transitory computer readable medium having stored thereon instructions, that when executed by one or more processors of a computing device, cause the computing device to perform functions comprising:
  receiving a data model constructed, at least in part, from protected health information (PHI) hosted by a corresponding health data provider, the received data model containing no PHI, wherein the data model includes clinical pathways representing sequences of health related events;
  creating a state transition machine from the received data model, wherein a state of the state transition machine represents a health related event of a synthetic life, and wherein a probability of transitioning from a first state to a second state is based on a health attribute and a disease prevalence statistic;
  generating a synthetic health data set comprised of a synthetic electronic health record (EHR) for each synthetic person in a synthetic population, wherein the synthetic EHR for each synthetic person is generated by calculating health related events for each time step in the synthetic life, and wherein the health related events are determined in part by the health attributes of each synthetic person at each time step;
  calculating a similarity score by comparing the generated synthetic health data set to an actual health data set including an actual EHR, wherein the actual health data set includes a health related event and associated time information for the health related event, where the health related event and associated time information are derived from the PHI hosted by the health data provider; and
  tuning the received data model based on the score indicating similarity falling below a threshold similarity, thereby creating a tuned data model by:
    representing the received data model as a probabilistic graphical model;
    determining probabilities of probabilistic graphical model based on the health related event from the actual health data set to infer a probability that a particular synthetic life will transition within the graph; and
    selecting a distribution probability based on interpreting the data model from the inferred graphical model probability to create updated clinical pathways in the tuned data model for use in the state transition machine.

* * * * *